(12) United States Patent
Smith et al.

(10) Patent No.: US 7,261,559 B2
(45) Date of Patent: Aug. 28, 2007

(54) SYRINGE DELIVERY SYSTEM FOR DISPENSING A DENTAL COMPOSITE OR OTHER HIGHLY VISCOUS MATERIAL

(75) Inventors: Wade Smith, Pleasant Grove, UT (US); Bruce S. McLean, Sandy, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 183 days.

(21) Appl. No.: 11/096,361

(22) Filed: Apr. 1, 2005

(65) Prior Publication Data

US 2006/0223027 A1    Oct. 5, 2006

(51) Int. Cl.
*A61C 5/04*   (2006.01)
(52) U.S. Cl. .......................................... 433/90; 433/89
(58) Field of Classification Search ............ 433/80–81, 433/89–90, 116; 604/207, 208, 209–211, 604/232–234, 189; 222/386, 390, 391, 46–48, 222/16, 18, 282, 283, 309, 310, 325, 326, 222/336; 401/194
See application file for complete search history.

(56) References Cited

U.S. PATENT DOCUMENTS

| | | | |
|---|---|---|---|
| 949,163 A | 2/1910 | Stapley | |
| 1,724,617 A | 8/1929 | Rapellin | |
| 2,052,296 A * | 8/1936 | Huntley | 222/390 |
| 2,283,915 A * | 5/1942 | Cole | 604/211 |
| 2,472,116 A | 6/1949 | Maynes | |
| 2,591,457 A | 4/1952 | Maynes | |
| 3,002,517 A | 10/1961 | Pitton | |
| 3,809,297 A | 5/1974 | Poulten | |
| 3,815,785 A * | 6/1974 | Gilmont | 222/46 |
| 3,890,971 A | 6/1975 | Leeson et al. | |
| 3,943,927 A | 3/1976 | Norgren | |
| 3,993,226 A | 11/1976 | Pavenick | |
| 4,294,125 A | 10/1981 | Lee | |
| 4,485,944 A | 12/1984 | Eichholz | |
| 4,560,352 A | 12/1985 | Neiimeister et al. | |
| 4,716,710 A | 1/1988 | Galy et al. | |
| 4,813,870 A * | 3/1989 | Pitzen et al. | 433/90 |
| 4,863,072 A | 9/1989 | Perler | |
| 4,997,300 A * | 3/1991 | Spivey et al. | 401/123 |
| 5,308,340 A | 5/1994 | Harris | |
| 5,387,103 A * | 2/1995 | Fischer | 433/89 |
| 5,599,314 A * | 2/1997 | Neill | 604/207 |
| 5,603,701 A * | 2/1997 | Fischer | 604/211 |
| 5,618,273 A * | 4/1997 | Fischer | 604/211 |

(Continued)

*Primary Examiner*—Cris Rodriguez
*Assistant Examiner*—Sunil K. Singh
(74) *Attorney, Agent, or Firm*—Workman Nydegger

(57) ABSTRACT

A syringe delivery system for dispensing a highly viscous material through a syringe delivery opening. The system includes a syringe barrel having a delivery opening, a plunger including a threaded shaft that threadably engages the syringe barrel for selectively dispensing a viscous material through the delivery opening, and a plunger gripping member in gripping communication with the plunger that includes means for sealing the threaded shaft of the plunger so as to prevent contamination by foreign matter. According to one embodiment, a sheath may be included that covers the threaded shaft of the plunger so as to hide the plunger beneath the sheath. The sheath provides a sealed environment for the threaded shaft so as to prevent entrance or contamination by foreign matter.

25 Claims, 7 Drawing Sheets

U.S. PATENT DOCUMENTS

| | | |
|---|---|---|
| 5,819,983 A * | 10/1998 | White et al. ............... 222/1 |
| 5,843,042 A | 12/1998 | Ren |
| 6,109,484 A | 8/2000 | Sueoka et al. |
| 6,161,734 A | 12/2000 | Winkler |
| 6,164,498 A * | 12/2000 | Faughey et al. ........... 222/309 |
| 6,235,004 B1 * | 5/2001 | Steenfeldt-Jensen et al. ............... 604/207 |
| 6,302,286 B1 * | 10/2001 | Witherspoon ............. 215/11.6 |
| 6,431,743 B1 | 8/2002 | Mizutani et al. |
| 6,450,720 B1 * | 9/2002 | Cai ........................... 401/193 |
| 6,569,122 B2 * | 5/2003 | Fischer et al. ............. 604/181 |
| 6,699,224 B2 | 3/2004 | Kirchhofer et al. |
| 6,712,794 B2 * | 3/2004 | Kust et al. ................. 604/224 |
| 6,789,750 B1 * | 9/2004 | Heldt ......................... 239/490 |
| 6,899,699 B2 * | 5/2005 | Enggaard ................... 604/246 |
| 7,056,308 B2 * | 6/2006 | Utterberg .................. 604/256 |
| 2002/0094506 A1 * | 7/2002 | Fischer et al. .............. 433/90 |
| 2003/0040716 A1 | 2/2003 | Heiniger et al. |
| 2003/0050606 A1 | 3/2003 | Brand et al. |
| 2003/0097096 A1 * | 5/2003 | Niedospial, Jr. ........... 604/218 |
| 2004/0073176 A1 | 4/2004 | Utterberg |
| 2004/0210199 A1 * | 10/2004 | Atterbury et al. .......... 604/224 |
| 2004/0210200 A1 | 10/2004 | Gerondale et al. |
| 2006/0192165 A1 * | 8/2006 | Matkovich et al. ...... 251/149.1 |

* cited by examiner

SYRINGE DELIVERY SYSTEM FOR DISPENSING A DENTAL COMPOSITE OR OTHER HIGHLY VISCOUS MATERIAL

BACKGROUND OF THE INVENTION

1. The Field of the Invention

The present invention relates to syringe systems that are used for storing and dispensing materials therefrom. More particularly, the present invention relates to a dental syringe system that provides for controllable doses of a highly viscous, pliable, light-activated dental composite.

2. The Relevant Technology

Cosmetic and/or functional augmentations of a tooth due to chipping or decay are common dental procedures. Typically, the dentist will apply a resin-based, light-activated dental composite to the tooth in order to fill a chipped or missing area. When the dental composite closely matches the natural color of the tooth, the repair job is barely, if at all, noticeable.

Typically, the dental composite is stored and dispensed from a syringe that is constructed to progressively extrude the composite material. Because the composite materials are highly viscous, it is often quite difficult to operate existing syringes without the use of both hands.

In addition, because only a small amount of the dental composite within a syringe is used for each patient, there is a risk of cross contamination from one patient to the next. In addition, existing syringes include numerous crevices that can make effective cleaning between patients difficult.

It would, therefore, be an advantage in the art to provide a syringe delivery system for dispensing a highly viscous material (e.g., a dental composite) having a design that is more effectively cleaned between patients. It would be a further advantage to provide a syringe delivery system that can be easily operated with only one hand.

BRIEF SUMMARY OF THE PREFERRED EMBODIMENTS

The present invention is directed to a syringe delivery system for dispensing a highly viscous material through a syringe delivery opening. The system includes a syringe barrel having a delivery opening, a plunger including a threaded shaft that threadably engages the syringe barrel for selectively dispensing a viscous material through the delivery opening, and a plunger gripping member in gripping communication with the plunger that includes means for sealing the threaded shaft of the plunger so as to prevent contamination by foreign matter. According to one embodiment, the means for sealing may comprise a sheath that covers the threaded shaft of the plunger so as to hide the plunger beneath the sheath. The sheath provides a sealed environment for the threaded shaft so as to prevent entrance or contamination by foreign matter.

According to one embodiment, at least one of the syringe barrel or sheath is ellipsoidal in cross section so as to allow a user to more easily grip the sheath and rotate the barrel during use.

The sheath may, in some cases, be enlarged relative to the syringe barrel. An enlarged sheath also allows a user to more easily grip the sheath and rotate the barrel during use.

To further facilitate easy gripping and one handed use, the syringe barrel and/or the sheath may include one or more gripping portions formed of a grippable material.

The syringe delivery system may further include a cap for selectively covering the delivery opening. In one example, the cap may comprise a flip-top cap.

According to one embodiment, the sheath of the plunger gripping member includes a window through which a level indicator is visible. The level indicator may comprise a tab formed as part of the threaded shaft of the plunger. The level indicator tab may ride within a groove formed on the inside surface of the sheath so as to be visible through the level indicator window. The groove may be located opposite the level indicator window (e.g., the groove is formed on an inside surface of the sheath adjacent to the level indicator window which allows a user to view a level indicator tab through the window). The position of the level indicator is dependent on the level of composite or other highly viscous material being dispensed. For example, when the system is full, the level indicator tab may be positioned at the proximal end of the groove formed within the inside surface of the sheath. As the material within the system is dispensed, the level indicator tab may ride within the groove towards an empty position.

According to one embodiment, the sheath and/or the syringe barrel may be formed of a material that blocks transmission of curing light wavelengths so as to prevent premature curing of a light curable dental composite or other curable material within the syringe barrel.

The syringe delivery system may further include a plurality of intersecting planar vanes at the distal delivery end of the syringe barrel so as to define separate compartments of the viscous material at the delivery opening. Such an embodiment allows a user to more easily dispense a desired amount of material. According to one embodiment, the intersecting planar vanes may comprise a material that blocks transmission of curing light wavelengths. Preferably, the intersecting planar vanes comprise a material that is sufficiently similar in color to the viscous material being dispensed, so as to be essentially unnoticeable in comparison to the viscous material. Such an embodiment prevents flecks of material removed from the planes that adhere to a dispensed material from being noticeable or distracting in the final cured material.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

A detailed description of the invention will now be provided with specific reference to Figures illustrating preferred embodiments of the invention. It will be appreciated that like structures will be provided with like reference designations.

The invention generally relates to a syringe delivery system for dispensing a viscous material through a syringe opening. The syringe delivery system includes a syringe barrel having a delivery opening, a plunger including a threaded shaft that threadably engages the syringe barrel for selective dispensing of a viscous material through the delivery opening, and a plunger gripping member in gripping communication with the plunger that includes means for sealing the threaded shaft of the plunger so as to prevent contamination by foreign matter. According to one embodiment, means for sealing may comprise a sheath that covers the threaded shaft of the plunger so as to hide the plunger beneath the sheath. The sheath provides a sealed environment for the threaded shaft so as to prevent entrance or contamination by foreign matter.

II. Exemplary Syringe Delivery Systems

Figure 1A:
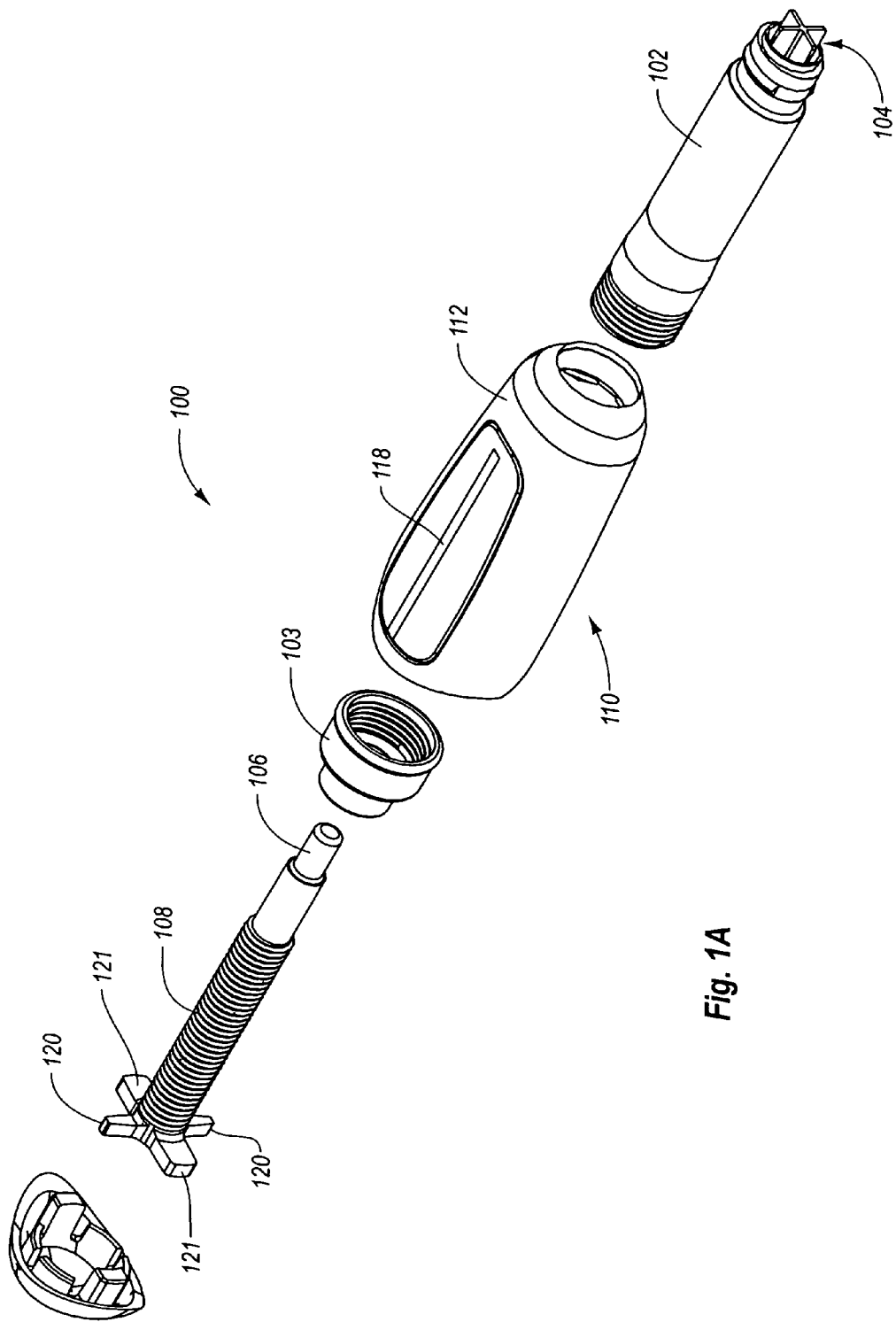
FIG. 1A is an exploded view of an exemplary syringe delivery system of the present invention.
Figure 1B:
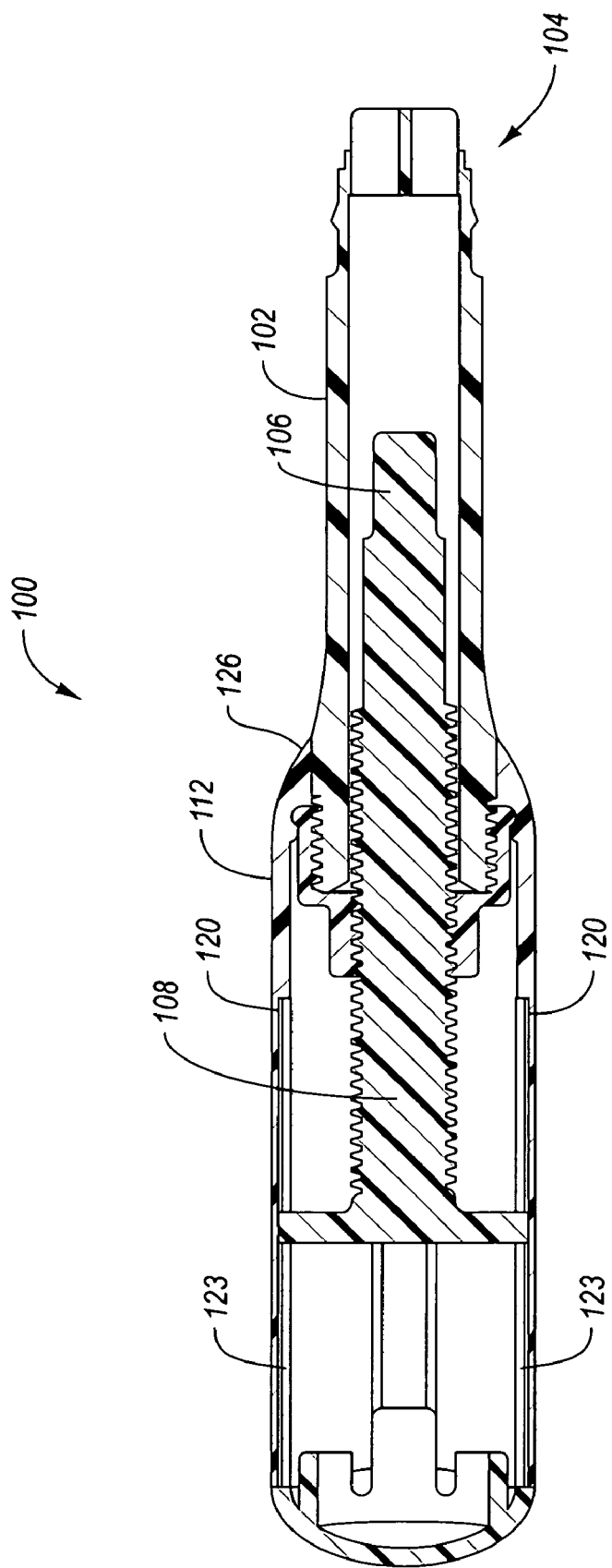
FIG. 1B is a cross sectional view of the assembled syringe delivery system of FIG. 1A.

FIGS. 1A and 1B illustrate, respectively, an exploded view and an assembled cross sectional view of a syringe delivery system 100. Syringe delivery system 100 includes a syringe barrel 102, having a delivery opening 104, a plunger 106 including a threaded shaft 108. The threaded shaft threadably engages a threaded nut 103 which itself threadably engages and may form part of syringe barrel 102, so as to allow a user to selectively dispense a viscous material through delivery opening 104.

Syringe delivery system 100 further includes a plunger gripping member 110. Plunger gripping member 110 is in gripping communication with plunger 106 via level indicator tabs 120 and gripping tabs 121 of plunger 106 and receiving grooves formed on an inside surface of plunger gripping member 110. Grooves 123, which mate with level indicator tabs 120, can be seen in FIG. 1B. Another pair of grooves (not seen) formed on an inside surface of plunger gripping member 110 mate with gripping tabs 121. Plunger gripping member 110 includes a sheath 112 that covers threaded shaft 108 of plunger 106, so as to shield plunger 106 and threaded shaft 108 beneath sheath 112. Sheath 112 provides a sealed environment for threaded shaft 108 so as to prevent entrance or contamination by foreign matter.

Figure 2:
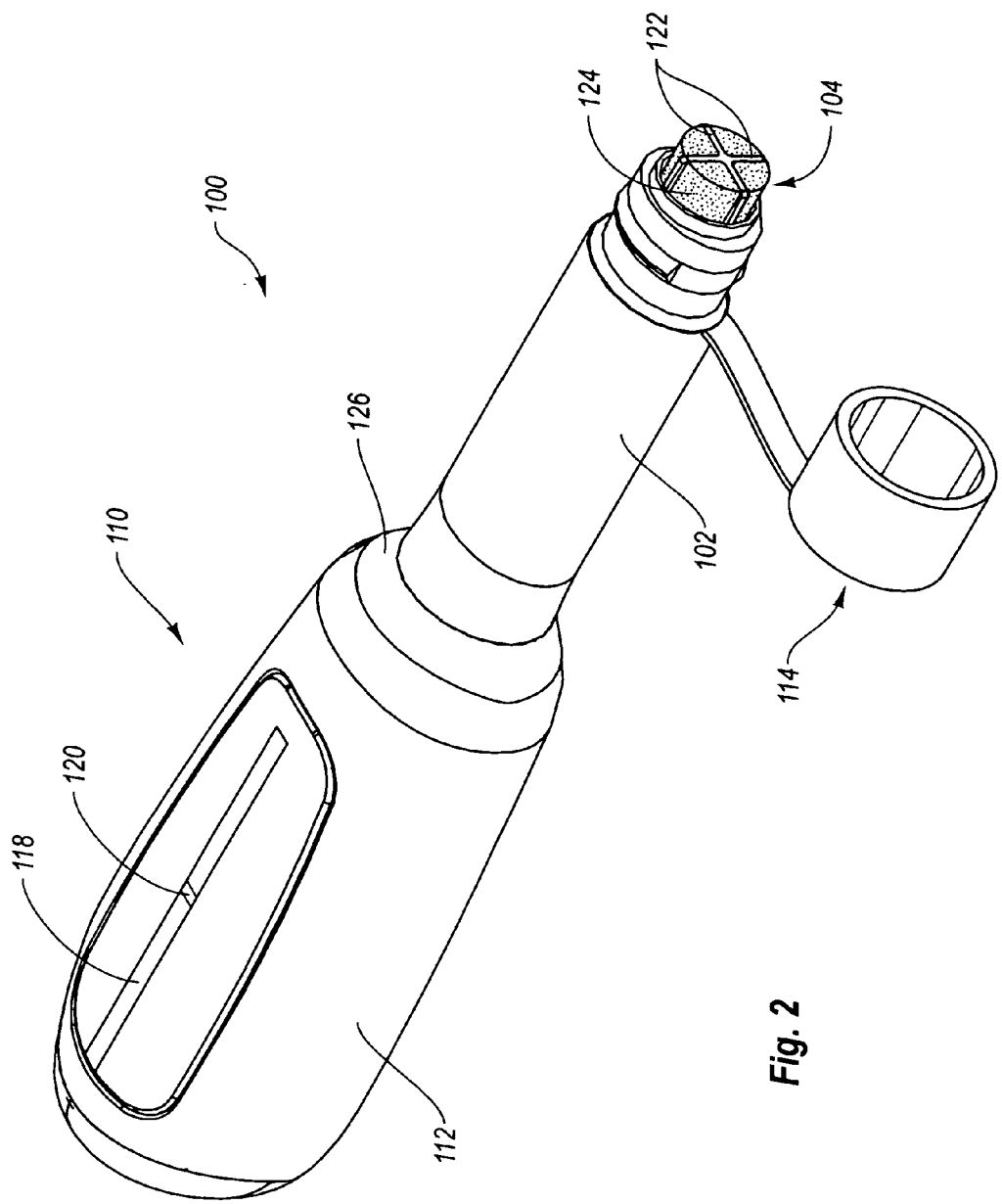
FIG. 2 is a perspective view of the syringe delivery system of FIG. 1A in an assembled configuration.

Perhaps as best seen in FIG. 2, at least one of syringe barrel 102 and/or sheath 112 may be a ellipsoidal in cross section. An ellipsoidal cross section in either the syringe barrel 102 or sheath 112 allows a user to more easily grip sheath 112 and rotate syringe barrel 102 during use, particularly during operation of the syringe delivery system 100 with only one hand. The embodiment illustrated in FIG. 2 includes an ellipsoidal sheath 112 and a cylindrical syringe barrel 102.

As illustrated in FIG. 2, sheath 112 may be enlarged relative to syringe barrel 102. Such a configuration also allows a user to more easily grip sheath 112 and rotate syringe barrel 102 during use, particularly during operation of the syringe delivery system 100 with only one hand.

To further aid in gripping and rotation, syringe barrel 102 may optionally include one or more gripping portions formed of a grippable material. According to one embodiment, the complete outside surface of syringe barrel 102 may be formed of a grippable material. According to one embodiment, the grippable material may comprise a thermoplastic elastomer. As illustrated, syringe delivery system 100 may further include a cap 114. FIG. 2 illustrates cap 114 as a flip-top cap, although any other suitable cap could be used.

According to one embodiment, the syringe delivery system 100 may include a level indicator window 118. Level indicator window 118 may be formed as a part of sheath 112. Window 118 may be formed of a suitable translucent or transparent material so as to allow a user to view the position of level indicator tab 120. According to one embodiment, the level of material within syringe barrel 102 may be indicated as full when level indicator tab 120 is near the proximal end of window 118. As the material within syringe barrel 102 is dispensed, tab 120 incrementally progresses towards the distal end of window 118. In other words, as syringe barrel 102 is rotated relative to sheath 112, threaded shaft 108 of plunger 106 to which tab 120 is attached also rotates relative to syringe barrel 102. causing the plunger 106 to move longitudinally relative to syringe barrel 102 and slide longitudinally within sheath 112. as the syringe barrel 102 does not move longitudinally relative to sheath 112 when rotated.

According to one embodiment, sheath 112 and/or syringe barrel 102 may comprise a material that blocks transmission of curing light wavelengths. According to one such embodiment, sheath 112 and syringe barrel 102 may be opaque.

According to one embodiment, syringe delivery system 100 further includes a plurality of intersecting planar vanes 122 at the distal end of syringe barrel 102. Intersecting planar vanes 122 define separate compartments of viscous material 124 as the material is pushed through syringe barrel 102 exiting through delivery opening 104. Intersecting planar vanes 122 may comprise any suitable material. According to one embodiment, planar vanes 122 comprise a material that blocks transmission of curing light wavelengths. According to a further embodiment, planar vanes 122 comprise a material that is sufficiently similar in color to the viscous material 124 being dispensed so as to be essentially unnoticeable in comparison to the viscous material. Such an embodiment prevents flecks of the planar vane material that may be removed with viscous material 124 from being noticeable in the cured material (e.g., dental restoration).

According to one embodiment, syringe delivery system 100 may include a dynamic seal 126 between plunger gripping member 110 and syringe barrel 102. Such a dynamic seal 126 may be formed of any suitable flexible material (e.g., a thermoplastic elastomer). The dynamic seal 126 forms a tight seal between plunger gripping member 110 and syringe barrel 102 so as to prevent entrance or contamination by foreign matter as syringe barrel 102 is rotated relative to plunger gripping member 110 during delivery of the dental composite or other highly viscous material.

Figure 3A:
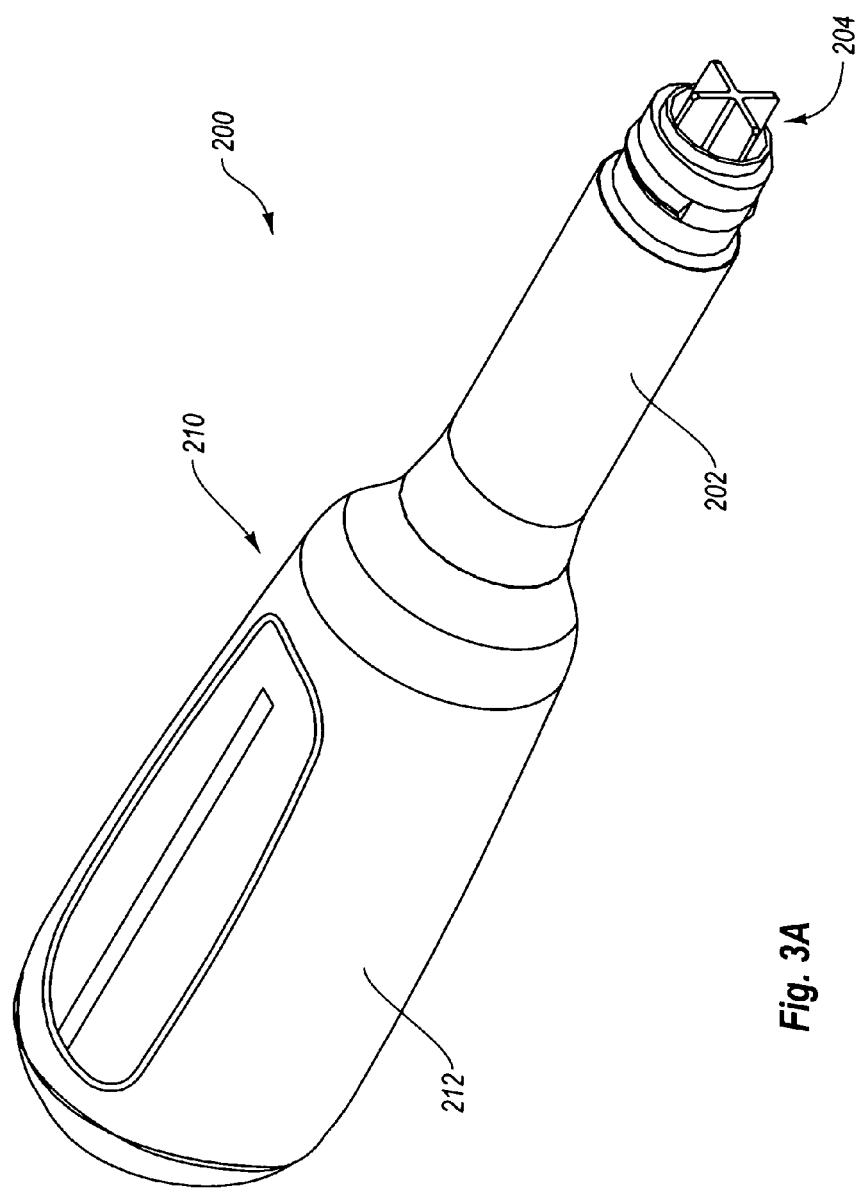
FIG. 3A is a perspective view of an alternative syringe delivery system having a cylindrical sheath and an ellipsoidal barrel.

FIG. 3A illustrates an alternative syringe delivery system 200. Syringe delivery system 200 includes a syringe barrel 202 having a delivery opening 204, a plunger including a threaded shaft (not seen) that threadably engages syringe barrel 202 for selectively dispensing a viscous material through delivery opening 204. Syringe delivery system 200 further includes plunger gripping member 210 including a cylindrical sheath 212. Sheath 212 provides a sealed environment for the threaded shaft (hidden beneath sheath 212), so as to prevent entrance or contamination by foreign matter. The sheath 212 of plunger gripping member 210 is illustrated as being cylindrical while syringe barrel 202 is illustrated as being ellipsoidal in cross section.

Figure 3B:
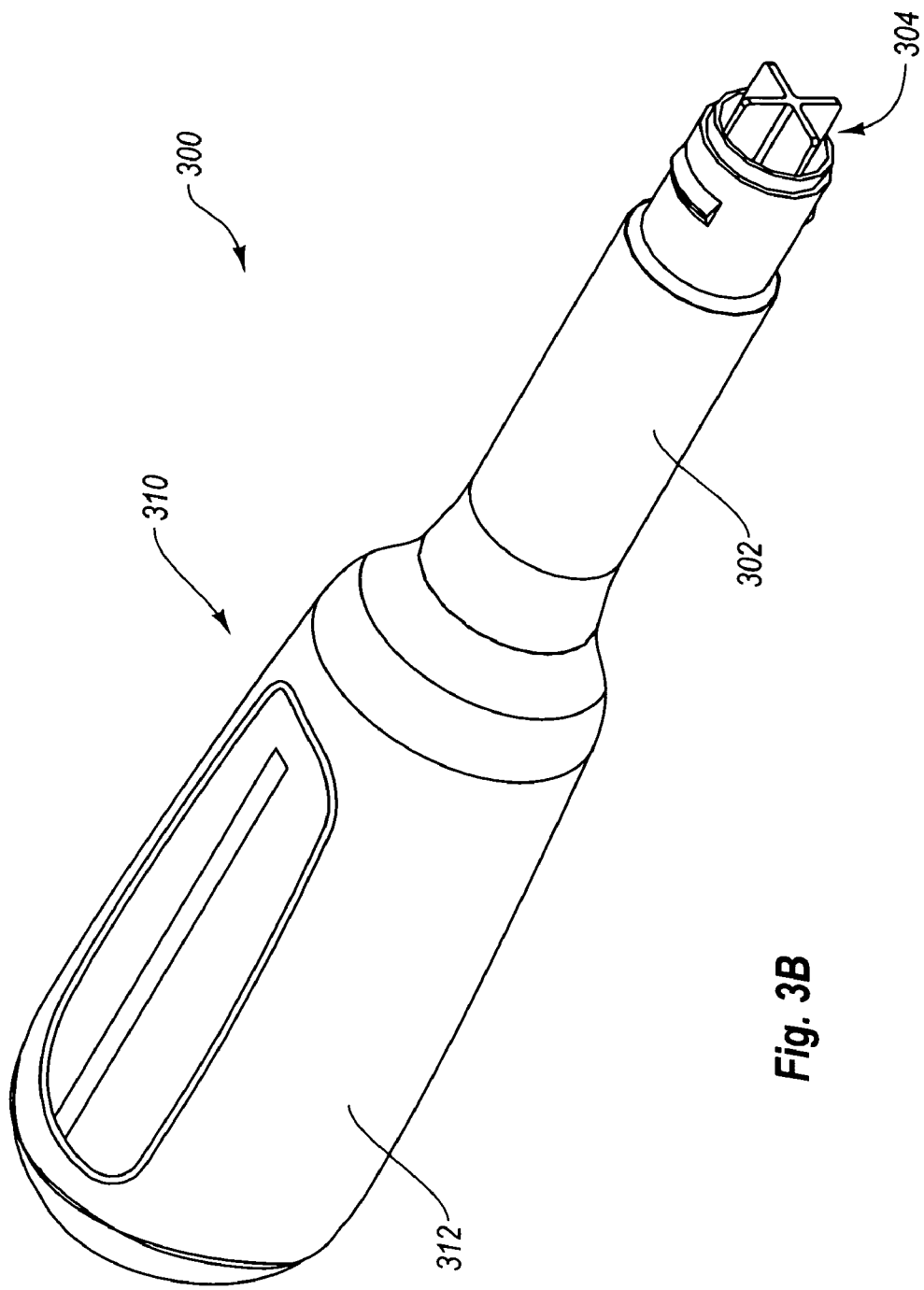
FIG. 3B is a perspective view of an alternative syringe delivery system having a cylindrical sheath and a cylindrical barrel.

FIG. 3B illustrates another alternative embodiment of a syringe delivery system where both the sheath and syringe barrel are cylindrical. Syringe delivery system 300 includes a syringe barrel 302 having a delivery opening 304, a plunger including a threaded shaft (not seen) that threadably engages syringe barrel 302 for selectively dispensing a viscous material through delivery opening 304, and a plunger gripping member 310 that includes a sheath 312. Sheath 312 covers the threaded shaft and plunger (not seen) so as to hide the plunger and threaded shaft beneath sheath 312. Sheath 312 provides a sealed environment for threaded shaft, so as to prevent entrance or contamination by foreign matter.

Although various embodiments have been illustrated including syringe barrels and/or sheaths of elliptical and/or cylindrical cross sections, it is to be understood that the sheath and/or syringe barrel may be of any shape desired.

III. Exemplary Methods of Use

Figure 4:
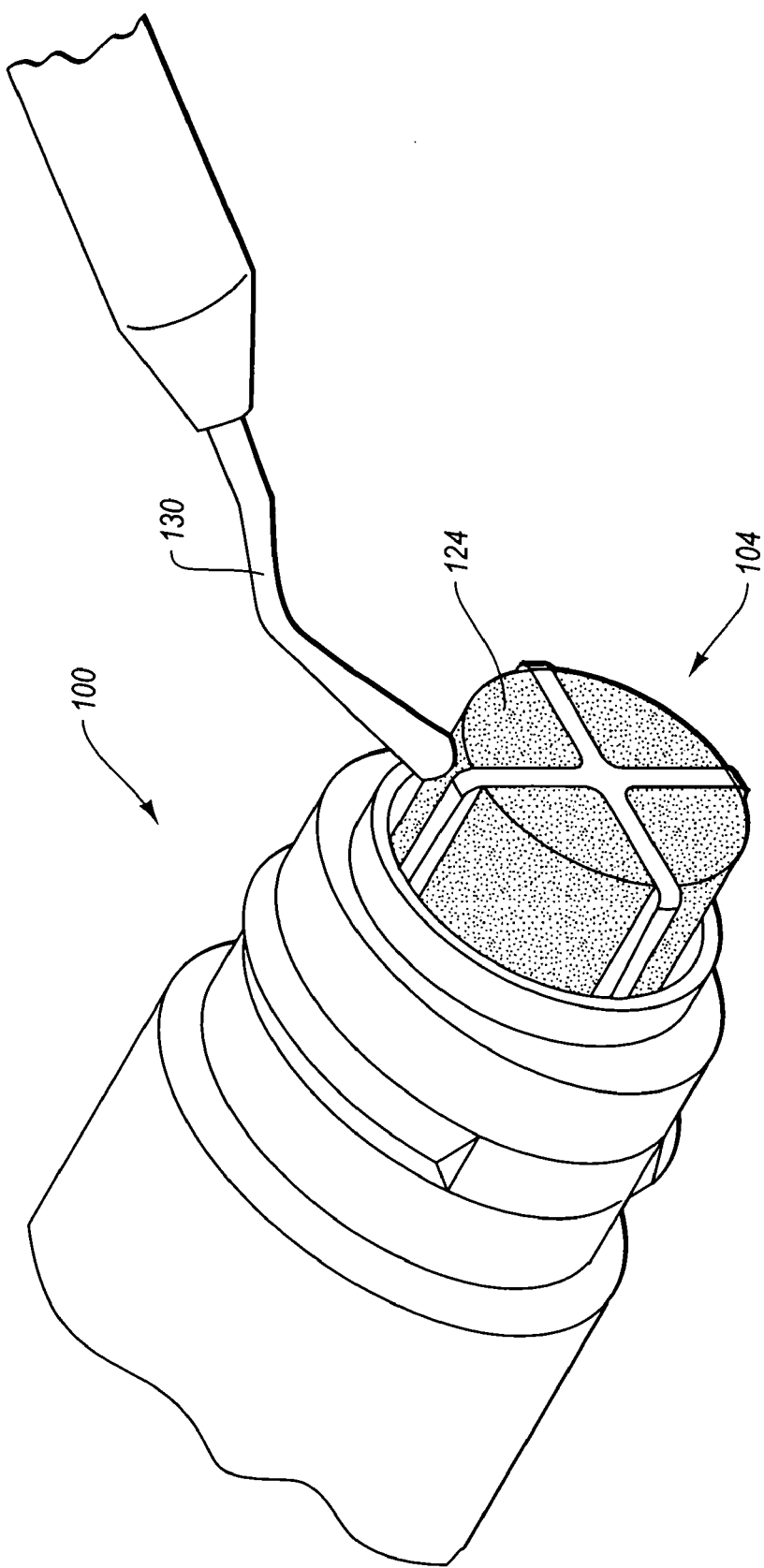
FIG. 4 is a close up partial perspective view of a desired amount of product being dispensed from the distal delivery end of an exemplary syringe delivery system.

FIG. 4 illustrates a method of using syringe delivery system 100 for dispensing a viscous material 124 through delivery opening 104. A dental instrument 130 may be used to remove a wedge or portion of viscous material for use. Once the desired amount of material has been removed, syringe delivery system 100 may be cleaned.

Figure 5:
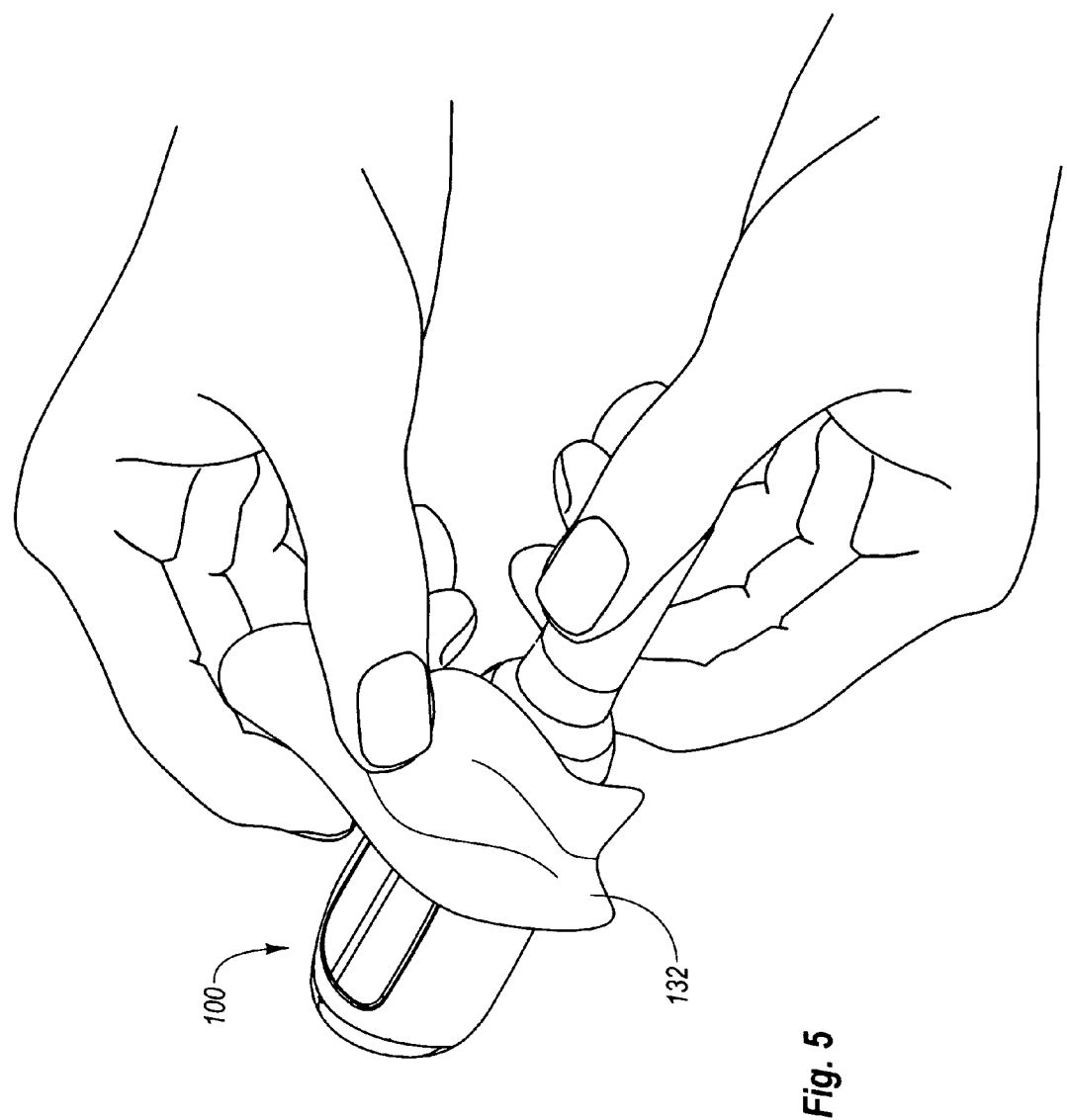
FIG. 5 is a perspective view of the syringe delivery system of FIG. 2 being wiped down for sterilization.

FIG. 5 illustrates syringe delivery system 100 being wiped down with a towelette 132 used to sanitize, clean, and disinfect syringe delivery system 100. Smooth and closed sheath 112 makes cleaning simple and effective. Because the sheath of syringe delivery system 100 completely covers the plunger and threaded shaft, foreign matter is prevented from entering and contaminating the syringe delivery system 100, particularly the small crevices of the threaded shaft.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A syringe delivery system for dispensing a viscous material through a syringe opening comprising:

a syringe barrel having an outer gripping surface that is at least partially exposed during use, a hollow inner chamber for holding therein a viscous material to be delivered, and a delivery opening at a delivery end of said syringe barrel in communication with said hollow inner chamber;

a threaded nut attached to or forming part of said syringe barrel;

a plunger including a threaded shaft that threadably engages said threaded nut and which is at least partially disposed within said hollow inner chamber of said syringe barrel for selective advancement within, and dispensing of a viscous material from, said hollow inner chamber through the delivery opening;

a plunger gripping member in gripping communication with said plunger comprised of a hollow sheath that is rotatable relative to the syringe barrel and which encloses said threaded shaft of said plunger and a portion of said outer gripping surface of said syringe barrel, said hollow sheath enclosing a portion of said outer surface of said syringe barrel as said plunger is advanced within said hollow inner chamber; and a dynamic seal comprised of a flexible elastomer material integrally formed on an inner surface of said hollow sheath that engages said outer surface of said syringe barrel, said dynamic seal remaining fixed relative to said hollow sheath and rotating relative to said syringe barrel as the sheath and barrel are rotated relative to each other, said dynamic seal remaining in contact with said outer surface of said syringe barrel to thereby maintain a seal between said hollow sheath and said outer surface of said syringe barrel so as to prevent entrance or contamination by foreign matter.

2. A syringe delivery system as recited in claim 1, wherein at least one of said barrel or said sheath is ellipsoidal in cross section so as to allow a user to more easily grip said sheath and rotate said syringe barrel with a single hand during use.

3. A syringe delivery system as recited in claim 2, wherein said sheath is ellipsoidal and said barrel is cylindrical.

4. A syringe delivery system as recited in claim 2, wherein said syringe barrel is ellipsoidal.

5. A syringe delivery system as recited in claim 1, wherein said sheath is enlarged relative to said syringe barrel.

6. A syringe delivery system as recited in claim 1, wherein said syringe barrel and/or said sheath comprise one or more gripping portions formed of a grippable material.

7. A syringe delivery system as recited in claim 1, wherein said threaded nut is threadably attached to an end of said syringe barrel distal to said dispensing end.

8. A syringe delivery system as recited in claim 1, further comprising a cap.

9. A syringe delivery system as recited in claim 8, wherein said cap comprises a flip-top cap.

10. A syringe delivery system as recited in claim 1, wherein said sheath of said plunger gripping member further comprises at least one level indicator window.

11. A syringe delivery system as recited in claim 10, wherein said threaded shaft includes at least one level indicator tab that rides within at least one groove formed on an inside surface of said sheath, said at least one groove being opposite said level indicator window.

12. A syringe delivery system as recited in claim 11, wherein said plunger further comprises at least one gripping tab that rides within at least one groove formed on an inside surface of said sheath, said plunger gripping member being in gripping communication with said plunger via said at least one level indicator tab and said at least one gripping tab of said plunger riding within said grooves formed on an inside surface of said plunger gripping member.

13. A syringe delivery system as recited in claim 1, wherein said sheath and said syringe barrel comprise a material that blocks transmission of curing light wavelengths.

14. A syringe delivery system as recited in claim 1, further comprising a plurality of intersecting planar vanes at the distal end of said syringe barrel for defining separate compartments of a viscous material as the material is pushed through said syringe barrel.

15. A syringe delivery system as recited in claim 14, wherein said intersecting planar vanes comprise a material that blocks transmission of curing light wavelengths.

16. A syringe delivery system as recited in claim 14, wherein said intersecting planar vanes comprise a material that is sufficiently similar in color to the viscous material being dispensed as to be essentially unnoticeable in comparison to the viscous material.

17. A method of using a syringe delivery system comprising:
providing a syringe delivery system as recited in claim 1,
manipulating said syringe delivery system so as to selectively dispense a viscous material through the delivery opening of said syringe delivery system; and
cleaning the syringe barrel and sheath of said syringe delivery system.

18. A method as recited in claim 17, wherein said syringe barrel and said sheath are cleaned with a towelette.

19. A syringe delivery system as recited in claim 1, wherein said flexible material of said dynamic seal comprises a thermoplastic elastomer.

20. A syringe delivery system for dispensing a viscous material through a syringe opening comprising:
a syringe barrel having an outer gripping surface that is at least partially exposed during use, a hollow inner chamber for holding therein a viscous material to be delivered, a delivery opening at a delivery end of said syringe barrel in communication with said hollow inner chamber, and a cylindrical distal end opposite said delivery end;
a threaded nut attached to or forming part of said syringe barrel;
a plunger including a threaded shaft that threadably engages said threaded nut and which is at least partially disposed within said hollow inner chamber of said syringe barrel for selective advancement within, and dispensing of a viscous material from, said hollow inner chamber through the delivery opening;
a plunger gripping member in gripping communication with said plunger comprised of a hollow sheath that is rotatable relative to the syringe barrel and which encloses said threaded shaft of said plunger and said cylindrical distal end of said syringe barrel so as to shield said plunger and said cylindrical distal end within said hollow sheath, said hollow sheath enclosing a portion of said cylindrical distal end of said syringe barrel as said plunger is advanced within said hollow inner chamber; and
a dynamic seal comprised of a flexible elastomer positioned so as to rotate relative to said sheath or said syringe barrel as the sheath and barrel are rotated relative to each other, said dynamic seal remaining in contact with said sheath and said outer surface of said syringe barrel to thereby maintain a seal between said hollow sheath and said outer surface of said syringe barrel and thereby prevent entrance or contamination by foreign matter,
said sheath being enlarged in cross section relative to a cross-section of said syringe barrel so as to facilitate relative rotation of said sheath and said syringe barrel;
wherein said sheath provides a protective environment for said threaded shaft.

21. A syringe delivery system as recited in claim 20, wherein said sheath is substantially larger in cross-section compared to said syringe barrel.

22. A syringe delivery system as recited in claim 20, wherein said flexible elastomer is formed on an inner surface of said sheath that engages said outer surface of said syringe barrel and/or on said outer surface of said syringe barrel that engages said inner surface of said hollow sheath so as to prevent entrance or contamination by foreign matter.

23. A syringe delivery system as recited in claim 22, wherein said flexible elastomer of said dynamic seal comprises a thermoplastic elastomer.

24. A syringe delivery system for dispensing a viscous material through a syringe opening comprising:
a syringe barrel having a delivery opening;
a plunger including a threaded shaft that threadably engages said syringe barrel for selective dispensing of a viscous material through the delivery opening; and
a plunger gripping member in gripping communication with said plunger that includes a sheath that covers said threaded shaft of said plunger so as to shield said plunger beneath said sheath;
wherein said sheath includes at least one level indicator window and said threaded shaft includes at least one level indicator tab that rides within at least one groove formed on an inside surface of said sheath, said at least one groove being adjacent to said level indicator window.

25. A syringe delivery system as recited in claim 24, wherein said plunger further comprises at least one gripping tab that rides within at least one groove formed on an inside surface of said sheath, said plunger gripping member being in gripping communication with said plunger via said at least one level indicator tab and said at least one gripping tab of said plunger riding within said grooves formed on the inside surface of said sheath.

* * * * *